US007419835B2

(12) United States Patent
Torres et al.

(10) Patent No.: US 7,419,835 B2
(45) Date of Patent: Sep. 2, 2008

(54) SCREENING FOR LIGAND BINDING AT SPECIFIC TARGET SITES

(75) Inventors: Francisco E. Torres, San Jose, CA (US); Richard H. Bruce, Los Altos, CA (US); Rodney Turner, San Francisco, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 780 days.

(21) Appl. No.: 10/719,457

(22) Filed: Nov. 21, 2003

(65) Prior Publication Data

US 2005/0112710 A1 May 26, 2005

(51) Int. Cl.
*G01K 17/20* (2006.01)
*G01N 35/00* (2006.01)
*G01N 25/20* (2006.01)

(52) U.S. Cl. .............. 436/147; 422/50; 422/51; 422/68.1; 422/82.12; 436/43; 436/174; 436/175; 436/180; 374/31; 374/32

(58) Field of Classification Search .......... 422/50, 422/68.1, 51, 82.12; 436/147, 180, 174, 436/175, 43; 374/31, 32
See application file for complete search history.

(56) References Cited

U.S. PATENT DOCUMENTS 6,294,063 B1 * 9/2001 Becker et al. ............... 204/450
6,380,605 B1   4/2002 Verhaegen ................... 257/467
6,545,334 B2   4/2003 Verhaegen ................... 257/467
2004/0038227 A1 * 2/2004 Verwaerde et al. ............ 435/6
2005/0076943 A1 * 4/2005 Cooper et al. ............... 136/224

OTHER PUBLICATIONS

Lehto et al. (WO 99/54730).*
U.S. Appl. No. 09/946,047, filed Sep. 4, 2001, Connelly et al.
U.S. Appl. No. 10/114,611, filed Apr. 1, 2002, Bell et al.
U.S. Appl. No. 10/115,336, filed Apr. 1, 2002, Elrod et al.
U.S. Appl. No. 10/303,446, filed Nov. 22, 2002, Bruce et al.
U.S. Appl. No. 10/303,500, filed Nov. 22, 2002, Bruce et al.
R. Seethala, P.B. Fernandes, eds, Handbook of Drug Screening, Marcel Dekker Inc., 2001.

* cited by examiner

*Primary Examiner*—Brian J Sines
(74) *Attorney, Agent, or Firm*—Fay Sharpe LLP (57) ABSTRACT

A method for screening of compounds for binding differentiation at various drug target binding sites is used with a device measuring the enthalpy of reaction for the binding. The method includes merging test ligand with target compound and merging test ligand with target compound in the presence of at least one blocking agent. A first heat of reaction is detected for the merged test ligand and target compound solution and a second heat of reaction is detected for the merged test ligand and target compound solution in the presence of a blocking agent. The two heats of reaction are compared to determine whether a reaction has occurred.

49 Claims, 5 Drawing Sheets

SCREENING FOR LIGAND BINDING AT SPECIFIC TARGET SITES

CROSS-REFERENCE TO RELATED APPLICATIONS

The following copending applications, U.S. application Ser. No. 10/114,611, filed Apr. 1, 2002, titled "Apparatus and Method for a Nanocalorimeter for Detecting Chemical Reactions"; U.S. application Ser. No. 10/115,336, filed Apr. 1, 2002, titled "Apparatus and Method for Using Electrostatic Force to Cause Fluid Movement"; U.S. application Ser. No. 10/303,446, filed Nov. 22, 2002, titled "Apparatus and Method for Lead Profiling Assay"; and U.S. application Ser. No. 10/303,500, filed Nov. 22, 2002, titled "Apparatus and Method for Multiple Target Assay for Drug Discovery", are assigned to the same assignee of the present application. The entire disclosures of these copending applications are totally incorporated herein by reference in their entirety.

INCORPORATION BY REFERENCE

The following U.S. patents are fully incorporated herein by reference: U.S. Pat. No. 6,380,605 to Verhaegen ("Device and a Method for Thermal Sensing"); U.S. Pat. No. 6,545,334 to Verhaegen ("Device and a Method for Thermal Sensing"); and U.S. application Ser. No. 09/946,047 to Connelly et al. ("Drug Discovery Employing Calorimetric Target Triage").

BACKGROUND

This disclosure relates generally to screening compounds for binding with targets, including drug targets, and more specifically to the differentiation of binding at different sites on targets, including drug targets, an example being differentiation of inhibitory binding at a specific substrate site and inhibitory binding at some other substrate, cofactor, regulator, or signaling site on an enzyme target.

Molecules that can inhibit or otherwise modify the activity of a drug target can be good drug candidates or leads, so there is a great deal of interest in screening compound libraries against drug targets to find such leads. For example, molecules that bind to an enzyme at a site that would otherwise bind a substrate or cofactor can slow down the reaction or even prevent the substrate from reacting. Additionally, a lead molecule that binds to an allosteric regulatory site can modify the enzymatic process, which could also be useful for therapeutic purposes. However, a good drug candidate also needs to be specific to the enzyme being targeted; it is generally not good therapeutically for a drug candidate to affect many different enzymes in a large class.

Enzymes, which are biomolecules that catalyze reactions between other molecules and are key to biological function, constitute one class of drug targets. In the enzymatic process, the enzyme binds the reacting molecule or molecules at specific binding sites, the case of two reacting molecules being the most common. For example, ATP kinases catalyze reactions between ATP (adenosine 5'-triphosphate) and a second, enzyme-specific substrate, resulting in a phosphorylated product and ADP (adenosine 5'-diphosphate). An enzyme may also bind cofactors that act to enable the enzyme function, as well as binding other inhibitors, effectors, or signaling partners. Thus, it is often the case that enzymes have more than one binding site that affects the rate of catalysis, including substrate sites, one or more cofactor sites, and other regulatory or signaling sites.

One way to screen for leads that are specific to a particular enzyme is to target a specific site on the enzyme that binds a substrate, cofactor, regulator, or signaling partner that is largely specific to the enzyme. As an example of this strategy, consider screening for binding to a protein kinase. ATP-dependent protein kinases catalyze reactions between ATP and a protein substrate, with the particular protein substrate being different for different protein kinases. Since ATP binding is common to all ATP kinases, a test compound that binds solely to the ATP-binding site on a target enzyme has a significant chance of binding to many other kinases. On the other hand, a test compound that binds to the same site as the protein substrate for that enzyme is a candidate for being more specific to that enzyme target. In this example, one would screen for binding to the same site as the protein substrate. This example can be extended to other kinases (e.g., non-protein substrates, ADP-dependent kinases and other non-ATP kinases) as well. Examples of targets other than kinases with multiple binding sites include G-proteins, which all hydrolyze GTP (guanosine 5'-triphosphate) but transfer signals between enzyme-specific GPCR (G-protein coupled receptor) regulators and downstream signaling targets; monomeric GTPases, which all hydrolyze GTP but signal specific molecules; and dehydrogenases, including those that use NAD+ (nicotinamide adenine dinucleotide), NADP+ (nicotinamide adenine dinucleotide phosphate), or FAD (flavin adenine dinucleotide) to dehydrogenate a second, enzyme-specific substrate.

More broadly, many proteins in any given family often share a common substrate, cofactor, regulator, or other ligand (such as an upstream or downstream signaling partner), while also having a different substrate, cofactor, regulator, or other ligand that is more specific to the protein of interest. Targeting the binding sites of the more specific ligands on protein drug targets can be useful in drug discovery.

In drug discovery today with enzyme targets, an endpoint assay is often used to determine if an enzymatic reaction has gone to completion, and in the initial high-throughput screening phase, as many as millions of drug candidates are screened using this type of assay. In such a screen, an inhibitor is added to the enzyme-cofactor-substrate mixture, and the mixture is tested for reaction. Today, the majority of high-throughput assays are designed to detect the converted substrate, i.e., they detect the endpoint of the enzymatic process (such as in the widely-used antibody-binding assays for protein phosphorylation). Such assays do not easily differentiate between binding of inhibitors at different sites. While follow-up kinetic studies and titration measurements of inhibitor activity can help differentiate between inhibitors that compete with a particular ligand for binding and those that do not, there is a pressing need to develop high-throughput methods that can easily and directly discriminate between binding at different binding sites, including as an example discriminating between competitive inhibition at different binding sites.

The need for high-throughput methods has increased in recent years as researchers and companies have turned to combinatorial methods and techniques for synthesizing, discovering and developing new compounds, materials, and chemistries. For example, pharmaceutical researchers have turned to combinatorial libraries as sources of new lead compounds for drug discovery. See *Handbook of Drug Screening* (R. Seethala and P. B. Fernandes, eds., Marcel Dekker Inc., 2001) for a review of progress in this area. The recent explosion in the number of potential drug targets due to the accelerated implementation of genomics technologies and the completion of the Human Genome sequence has only increased the need to develop effective high-throughput methods for screening against drug targets. Combinatorial methods are also being applied to other industries, as illustrated by companies such as Symyx Technologies® that is applying combinatorial techniques to materials discovery in the life sciences, chemical, and electronics industries.

To further illustrate the use of combinatorial chemistry methods and the need for improved methods, we now discuss the example of pharmaceutical research in this area in more detail. Pharmaceutical researchers have turned to combinatorial libraries as sources of new lead compounds for drug discovery. A combinatorial library is a collection of chemical compounds that have been generated, by either chemical synthesis or biological synthesis, by combining a number of chemical "building blocks" as reagents. For example, a combinatorial polypeptide library is formed by combining a set of amino acids in every possible way for a given compound length (i.e., the number of amino acids in a polypeptide compound). Millions of chemical compounds can theoretically be synthesized through such combinatorial mixing of chemical building blocks.

Once a library has been constructed, it must be screened to identify compounds which can be used as leads to design drug candidates possessing some kind of biological or pharmacological activity. For example, screening can be done with a specific biological compound, often referred to as a target, which participates in a known biological pathway or is involved in some regulatory function. The library compounds that are found to react with the targets are candidates for affecting the biological activity of the target, and hence can be useful leads for developing a candidate for a therapeutic agent.

Since combinatorial methods involve looking at a large number of compounds and reactions in parallel, there is a need for tools that can measure reactions and interactions of large numbers of small samples in parallel, consistent with the needs of combinatorial discovery techniques. Preferably, users desire that these tools enable inexpensive measurements and minimize contamination and cross-contamination problems.

One method for measuring reactions and interactions is calorimetry. Calorimetry can be used to measure the thermodynamics and kinetics of reactions without requiring that reactants be labeled (e.g., radio-labeled or labeled with fluorophores) or immobilized on surfaces. Most other current methods require some modification of either the substrate or a cofactor (fluorescent labeling, surface anchoring, etc.) [*Handbook of Drug Screening*, R. Seethala and P. B. Fernandes, eds., Marcel Dekker Inc., 2001]. These modifications add steps and cost to an assay, and they can potentially modify the reagents in undesired ways that may not be understood at the time of an assay. Furthermore, it would be useful to have a method capable of replacing the cost of antibodies that are used in many enzyme endpoint assays, as it is largely the single largest cost contributor to overall screening cost. Calorimetry does not rely on antibody binding to products of enzymatic reactions.

In some cases, the sample to be studied is precious, and it might not be acceptable to use the relatively large amount of material required by a standard microcalorimeter to perform only one measurement. For example, one may desire to study a natural extract or synthesized compound for biological interactions, but in some cases the available amount of material at concentrations large enough for calorimetry might be no more than a few milliliters. Performing a measurement in standard microcalorimeters, such as those sold, for example, by MicroCal® Inc. (model VP-ITC) or Calorimetry Sciences Corporation® (model CSC-4500), requires about 1-2 ml of sample, which means that one would possibly be faced with using a majority or all of the precious material for one or a small series of measurements. Tools that enable calorimetric measurements with much smaller sample sizes would be helpful in overcoming this limitation. Furthermore, standard microcalorimeters require hours for one measurement, whereas high-throughput screening requires orders of magnitude higher throughput.

In drug development activities, it is sometimes the case that a strongly binding drug lead was discovered for a particular drug target, only to have it later determined that the drug lead is not specific enough to the target or has other drawbacks that render it not useful for further drug development. In such cases, investigators may chose to reinvestigate the drug target and look for drug hits or leads that bind to sites on the target other than the binding site for the previously discovered drug lead. As an example, investigators have sometimes found inhibitors of ATP kinases that are strong binders to the ATP binding site, only to learn that the inhibitors are not sufficiently specific to the kinase of interest, or otherwise bind or interact with other molecules in a way that produces adverse effects. One approach that an investigator may take in such a case is to reinvestigate the drug target to find drug hits or leads that bind to sites other than the ATP binding site. There is a need for high-throughput screening methods that allow investigators to screen for binding to a site other than the binding site of a previously discovered strongly binding ligand. In particular, there is a need for such methods that are also generic in the sense that they do not require labeling (e.g., fluorescent, chemiluminescent, or radio-labeling) of compounds, immobilization of compounds on surfaces, or other assay-specific modifications of the molecules being studied.

BRIEF SUMMARY

The disclosed embodiments provide examples of improved solutions to the problems noted in the above Background discussion and the art cited therein. There is shown in these examples an improved method for screening of compounds for binding differentiation at various drug target binding sites, which is used with a device measuring the enthalpy of reaction for the binding. The method includes merging test ligand with target compound and merging test ligand with target compound in the presence of a blocking agent. A first heat of reaction is detected for the merged test ligand and target compound solution and a second heat of reaction is detected for the merged test ligand and target compound solution in the presence of at least one blocking agent. The two heats of reaction are compared to determine whether a reaction has occurred.

In another embodiment there is disclosed a method for screening of compounds for binding differentiation at various drug target binding sites for use with a nanocalorimetric device measuring the enthalpy of reaction for the binding. The nanocalorimetric device includes thermal isolation regions, reference regions, and measurement regions. The method includes depositing target compound and a drop of test compound at different locations within a measurement region of the nanocalorimetric device. Within a reference region of the nanocalorimeter, target compound and test compound solution are deposited at different locations. The materials within the measurement region are merged and the materials within the reference region are merged in the presence of a blocking agent. The heats of reaction for each of the regions is detected and compared to determine whether a reaction has occurred.

BRIEF DESCRIPTION OF THE DRAWINGS

The foregoing and other features of the embodiments described herein will be apparent and easily understood from a further reading of the specification, claims and by reference to the accompanying drawings in which:

DETAILED DESCRIPTION

As used herein, the term "ligand" refers to an agent that binds to a target compound. According to the present disclosure, a ligand is not limited to an agent that binds to a recognized functional region of the target compound, e.g., the active site of an enzyme, the antigen-combining site of an antibody, the hormone-binding site of a receptor, a cofactor-binding site, and the like. In practicing the present disclosure, a ligand can also be an agent that binds any surface or conformational domains of the target compound. Therefore, the ligands of the present disclosure encompass agents that in and of themselves may have no apparent or known biological function, beyond their ability to bind to the target in the manner described above. The term ligand encompasses agents that react upon binding and agents that do not react other than by binding.

As used herein, the term "test ligand" refers to an agent, comprising a compound, molecule or complex, which is being tested for its ability to bind to a target compound. Test ligands can be virtually any agent, including without limitation metals, peptides, proteins, lipids, polysaccharides, nucleic acids, small organic molecules, synthetic organic compounds, and combinations thereof. Complex mixtures of substances such as natural product extracts, which may include more than one test ligand, can also be tested, and the component that binds the target can be purified from the mixture in a subsequent step.

As used herein, the term "enzyme" refers to an agent that catalyzes reactions in biological systems. Most known enzymes are proteins, but other biomolecules, such as catalytically active RNA, can also function as enzymes and are included in the scope of this definition. Examples of classes of enzymes include kinases, phosphatases, proteolytic enzymes, GTPases, ATPases, polymerases, RNases, DNases, and more generally oxidoreductases, transferases, hydrolases, lyases, isomerases, and ligases. Some enzymes require more than one protein molecule to be active (i.e., multimeric enzymes). In such cases, the complex as a whole is termed an enzyme unless specified otherwise.

As used herein, the term "substrate" refers to a reactant in an enzymatic reaction that is converted into a product. "Surrogate substrates" are one type of substrate, and they are termed surrogates because they can be used in assays in place of a naturally occurring substrate.

As used herein, the term "cofactor" refers to an agent that is necessary for an enzyme to be catalytically active, such as prosthetic groups and coenzymes, and which is not consumed in the process, meaning it is found unchanged at the end of the enzymatic reaction.

As used herein, the term "regulator" refers to a molecule that alters the activity of an enzyme. This terms encompasses inhibitors (competitive and non-competitive) and effectors. This term also encompasses regulators that bind allosterically.

As used herein, the term "signaling partner" refers to a molecule that binds with a protein as part of a signaling pathway. In this context, signaling partners includes protein or non-protein agents that bind with an enzyme to initiate, accelerate, or decelerate a reaction or series of reactions that involve the enzyme, and signaling partners also includes protein or non-protein agents to which an enzyme binds to initiate, accelerate, or decelerate a downstream reaction, series of reactions, or pathway.

As used herein, "screening" refers to the testing of a multiplicity of molecules or compounds for their ability to bind to a target.

As used herein, the term "biological target" encompasses peptides, proteins, nucleic-acids, protein-nucleic acid complexes, and other receptors. The term encompasses both enzymes and proteins which are not enzymes. The term encompasses monomeric and multimeric proteins and enzymes. Multimeric proteins and enzymes may be homomeric or heteromeric. The term encompasses nucleic acids comprising at least two nucleotides, such as oligonucleotides. Nucleic acids can be single-stranded, double-stranded, or triple-stranded. The term encompasses a nucleic acid which is a synthetic oligonucleotide, a portion of a recombinant DNA molecule, or a portion of chromosomal DNA. The term biological target also encompasses portions of peptides, secondary, tertiary, or quaternary structure through folding, with substituents including, but not limited to, cofactors, coenzymes, prosthetic groups, lipids, oligosaccharides, or phosphate groups.

As used herein, the term "target compound" encompasses biological targets, as well as other compounds that are targets for binding of one or more additional compounds. As used herein, the terms "target compound" and "target" are synonymous.

As used herein, the term "enzyme-specific substrate" refers to a substrate that is specific to the particular enzyme, to distinguish it from substrates common to a family of enzymes. For example, most protein kinases use ATP as one substrate, and the other substrate, a protein, is specific to the particular protein kinase of interest. In this case, ATP is not an enzyme-specific substrate because it is not specific to any one kinase or small fraction of kinases, but the protein substrate is an enzyme-specific substrate. Enzyme-specific substrates may be substrates for more than one enzyme. As used herein, they are still considered enzyme-specific as long as the number of enzymes in one class (e.g., kinases) that share the particular substrate is smaller than the number of enzymes in the class as a whole. The term "kinase-specific substrates" refers to enzyme-specific substrates in the case where the enzyme is a kinase. Examples of enzyme-specific substrates include glucose for hexokinase, fructose 6-phosphate for phosphofructokinase, and glucose-6-phosphate for phosphoglucose isomerase.

As used herein, the term "thermal change" encompasses the release of energy in the form of heat or the absorption of energy in the form of heat.

As used herein, the term "merging of a target compound" refers broadly to placing the target compound in solution with the test ligand to be screened for binding or reaction. Less broadly, merging refers to the turning, swirling, shaking or vibrating of a solution of the target compound and the test ligand to be screened for binding. More specifically, merging refers to the mixing of the target compound with the test ligand to be tested for binding. Mixing can be accomplished, for example, by repeated uptake and discharge through a pipette tip or by deposition by robotic means. Other means can also be used to bring the samples together, and are fully contemplated here and in the claims. For example, fluids may be brought together near the thermal sensors by drop translation along a support, or either drop, continuous fluid, or fluid packet translation through a channel or channels, including fluidic channels fabricated in devices using, for example, MEMS, "soft lithography", or other biochip fabrication techniques. Preferably, merging refers to the equilibration of binding between the target compound and the test ligand to be tested for binding.

The present disclosure encompasses nanocalorimeters and nanocalorimeter arrays that enable measurement of enthalpic changes, such as enthalpic changes arising from binding events, reactions, phase changes, changes in molecular conformation, and the like. For the purposes herein, a nanocalorimeter refers to a device capable of measuring heats of reaction in the range of nanocalories or higher, for example, with sensitivity limits of approximately 0.01 nanocalories to 10000 nanocalories. Furthermore, the present disclosure encompasses combinatorial methods and high-throughput screening methods that use nanocalorimeters in the study, discovery, and development of new compounds, materials, chemistries, and chemical processes, as well as high-throughput monitoring of compounds or materials, or high-throughput monitoring of the processes used to synthesize or modify compounds or materials. The present disclosure also relates to compounds or materials identified by the above methods and their therapeutic uses (for diagnostic, preventive or treatment purposes), uses in purification and separation methods, and uses related to their novel physical or chemical properties.

As an example, the present disclosure encompasses high-throughput screening methods for identifying a ligand that binds a target compound. If the target compound to which the test ligand binds is associated with or causative of a disease or condition, the ligand may be useful for diagnosing, preventing or treating the disease or condition. A ligand identified by the present method can also be one that is used in a purification or separation method, such as a method that results in purification or separation of the target compound from a mixture. The present disclosure also relates to ligands identified by the present method and their therapeutic uses (for diagnostic, preventive or treatment purposes) and uses in purification and separation methods. As an example, the present disclosure relates to proteins that are enzymes, as well as non-protein enzymes, such as ribozymes.

In practicing the present disclosure, the test ligand is combined with a target compound, and the mixture is maintained under appropriate conditions and for a sufficient time to test for binding of the test ligand to the target compound. In a different test site, the same test ligand is combined with the same target compound in the presence of an excess amount of an agent that competes with binding to a specific site on the target, or otherwise retards or blocks binding to a specific site on a target. Such an agent is termed a blocking agent. The difference between binding in the absence versus presence of the excess amount of the blocking agent, such as a blocking substrate, signals whether there is binding of the test ligand that competes with the agent. Specifically, if the test ligand binds at the same site as the blocking agent, then it will bind less in the presence of the excess of the blocking agent than in its absence, producing a differential signal.

Conversely, if the test ligand binds at another site that is not affected by the blocking agent, then the presence or absence of the blocking agent has no effect, thereby producing no differential signal. Experimental conditions are determined empirically for each system. When testing multiple test ligands, incubation conditions are usually chosen so that most ligand:target compound interactions would be expected to proceed to completion. In high-throughput screening applications, the test ligand is usually present in molar excess relative to the target compound. The target compound can be in a soluble form, can be in a cell membrane, membrane fragment, synthetic membrane, vesicle, organelle or organelle fragment, synthetic organelle or organelle fragment, micelle or equivalent heterogeneous environment, or, alternatively, can be bound to a solid phase. The matrix of the solid phase may comprise without limitation beads, membrane filters, plastic surfaces, or other suitable solid supports.

It can be appreciated that in some cases blocking agent may be present in both test sites discussed above, for example due to difficulty in removing a component in its entirety. A differential signal is still possible when blocking agent is present in the first test site mentioned above, as long as the blocking agent is less effective in the said first test site, for example due to a significantly lower concentration or other difference in properties, than in the second test site. Such instances are fully contemplated by the specification and scope of the claims herein.

The fact that the present method is based on physicochemical properties common to many proteins and most enzymes gives it widespread application. The present disclosure can be applied to large-scale systematic high-throughput procedures that allow a cost-effective screening of many thousands to millions of test ligands and target compounds. Once a target-ligand pair has been identified by the methods of the present disclosure, it can be further analyzed in more detail using known methods specific to the particular target used.

For the purposes of the discussion herein, embodiments of a nanocalorimeter are used to illustrate the operation of the assay sample preparation and analysis method. However, those skilled in the art will readily appreciate that the method may be employed beneficially on other nanocalorimeter configurations as well as microcalorimeter configurations, all of which are fully contemplated by the specification and scope of the claims herein.

Figure 1:
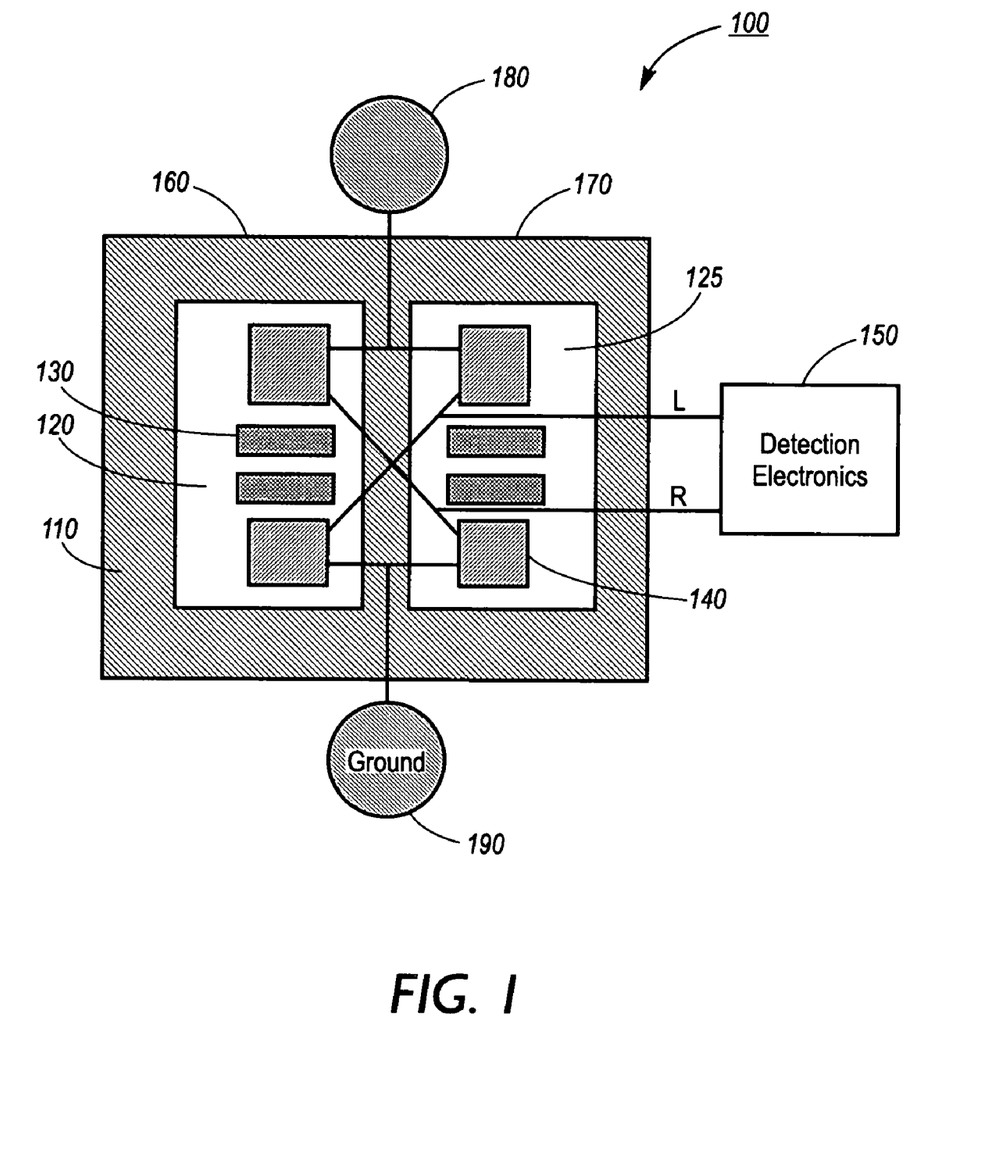
FIG. 1 is a block diagram depicting components of one embodiment of a nanocalorimeter utilized in practicing the method herein.

Referring now to FIG. 1, there is shown a plan view of one embodiment of detector 100 that is a part of one embodiment of a nanocalorimeter array which may be utilized in accordance with the method herein. This example embodiment enables a passive thermal equilibration of the protein, water and ligand drops with the device both before and after drop merging, so that the resultant temperature changes can be detected by means of a temperature sensing element. Because the measurement region is kept small enough and sufficiently thermally conductive, through the fabrication of a thermally conducting layer such as aluminum or copper, the passive equilibration time can be made small. This sample embodiment of a nanocalorimeter is described in more detail in U.S. application Ser. No. 10/114,611, "Apparatus and Method for a Nanocalorimeter for Detecting Chemical Reactions", incorporated by reference hereinabove.

Some of the features of this embodiment of a nanocalorimeter will be briefly described to facilitate understanding of the method presented herein, but it will be understood that this is only one example embodiment of a suitable nanocalorimeter to be used in practicing the method herein, which may be beneficially applied in various embodiments with various forms of nanocalorimeter, all of which are fully contemplated by the scope of the specification and claims herein. Nanocalorimeter 100 includes thermal isolation layer 110, which contains measurement region 160 and reference region 170. Regions 160 and 170 may also be contained in separate isolation regions. Thermal isolation region 110, along with the vapor phase surrounding regions 160 and 170, provides isolation from surrounding thermal environments, thus increasing measurement time and reducing thermal noise. Although layer 110 is used in this example embodiment to thermally isolate the reaction and temperature sensing components of the nanocalorimeter 100, any means to thermally isolate these components can be used in alternate embodiments of the present method. It should be understood that the thermal isolation does not need to be absolute; rather, it serves the purpose of slowing down heat losses, even when not stopping such losses altogether.

As suggested above, the thermal equilibration regions may be thermally isolated from their environment so that the temperature difference caused by the reaction takes a relatively long time to dissipate. The longer this dissipation time, the longer the signal can be integrated during measurement, which improves the signal to noise ratio.

Measurement region 160 and reference region 170 include thermal equilibration regions 120 and 125 respectively, which are thermally isolated from the detector's mechanical support. In this example embodiment, thermal equilibrium region 120 contains two resistive thermometers 140, which measure the reaction temperature, while thermal equilibrium region 125 contains a second set of two thermometers 140, which measure the variations in the reference temperature. The resistive thermometers are deposited in thermal equilibrium regions 120 using standard fabrication techniques, including in embodiments, but not limited to, lithographic patterning of thin films, micro-electronic fabrication techniques (e.g., including sputtering, chemical etching, evaporation), and printed circuit board fabrication techniques. Both thermal equilibrium regions 120 and 125 are sufficiently large to receive and support separate drops of protein and ligand, deposited for example by direct printing or other drop deposition techniques, and also to support the combination of these two drops after merging, triggered by an example drop merging device 130. For example, for a 400 nL final drop size, the detector, which includes the measurement and reference regions, may be 3.7 mm by 4.6 mm. Each thermal equilibration region 120 and 125 has a sufficient thermal conduction for the region to equilibrate quickly relative to the thermal dissipation of heat to the surroundings.

Each thermal equilibration region 120 and 125 contains thermometers 140 and drop merging electrodes 130. Although for the purposes herein thermometers 140 are shown spaced apart from more centrally-positioned drop merging electrodes 130 on each thermal equilibration region 120 and 125, this configuration is for means of example only. Provided that the drop merging device 130 and thermometers 140 are in good thermal contact with the high conductance film, the exact placement of thermometers 140 and drop merging electrodes 130 is not important for thermal considerations.

In operation, the two resistive thermometers 140 situated in thermal equilibration region 120 detect the heat of reaction between an arbitrary protein and a ligand at low concentrations deposited within thermal equilibration region 120. In this example, the heat of reaction is detected through measurement of a voltage change in a bridge circuit due to the resistance change in the thermometers which are configured in the bridge circuit. Resistive thermometers 140 in thermal equilibrium region 120 detect a reaction between a sample ligand and a protein; the other resistive thermometers 145 in thermal equilibrium region 125 serve as a reference. As a result, the signal from the bridge circuit detects the difference between the heats evolved in thermal equilibration region 120 and thermal equilibration region 125. As this disclosure describes a method for differentiation of binding at different sites on a target compound by measuring and comparing the binding in the absence and presence of agent that blocks or retards binding at a specific site on a target compound, bridge circuits like the one described are useful because they enable direct detection of the desired differential binding signal.

As an embodiment, the method disclosed herein utilizes nanocalorimetry in the identification of target-ligand pairs. Nanocalorimetry, such as described in U.S. application Ser. No. 10/114,611 ("Apparatus and Method for a Nanocalorimeter for Detecting Chemical Reactions"), is useful for this purpose because it directly detects the heat of reaction upon binding of a ligand to a target. No attachment of tags, such as fluorescent, chemiluminescent, or radio-labeled tags, or other special formatting or immobilization of the ligands or targets is necessary.

Figure 2:
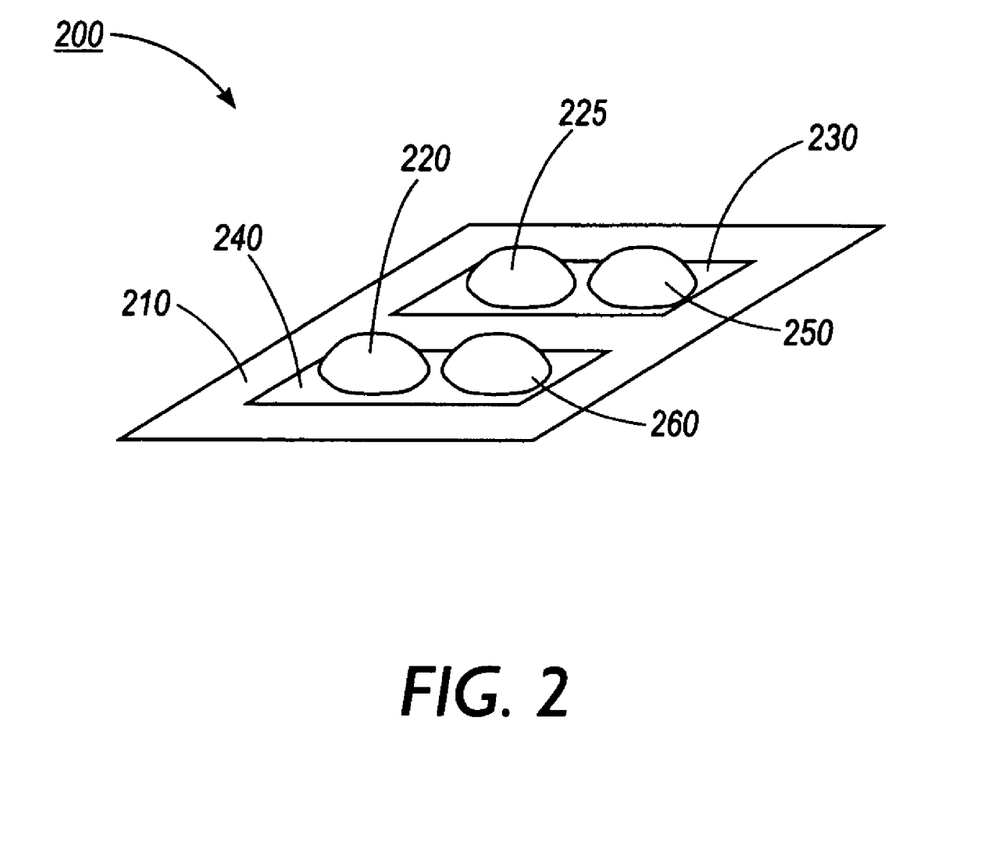
FIG. 2 is an illustration depicting enzyme and ligand drop deposition within a single cell of a testing array, according to one embodiment of the method.

Turning now to FIG. 2, there is shown one embodiment of drop deposition within a single nanocalorimeter cell 200 of an example test device, which may be part of a larger test array configuration. In this embodiment, both reference region 230 and measurement region 240 reside within thermal isolation region 210. The nanocalorimeter cell directly measures the difference in heating between the measurement and reference sides upon merging of the drops in the respective regions. In this embodiment, a drop 260 with the target compound of interest, an enzyme target being an example, and a separate drop 220 with a test ligand are placed on the measurement region of the nanocalorimeter cell. On the reference side is placed a drop 250 containing the target compound of interest and an agent that retards or blocks binding to a specific site on the target. In addition, on the reference side is placed a drop 225 containing the same test ligand as is in drop 220, at the same or nearly same concentration, and the same agent that retards or blocks binding to a specific site on the target as in drop 220, at the same or nearly same concentration. The purpose of including the blocking agent in drop 225 is to minimize heats of mixing or enthalpic changes arising from interactions of the test ligand and the blocking agent. In cases where these effects are small, or otherwise taken into account in the measurement or subsequent analysis of data, the blocking agent need not be present in drop 225. As examples, the target can be an enzyme, and the agent that retards or blocks binding to a specific site on the target can be a large excess of substrate, cofactor, inhibitor, or regulator that binds to the specific site of interest. Drop size may range from approximately 100 pL to approximately 100 μL. For the purposes of use with this embodiment of the nanocalorimeter, drop size may range from approximately 100 pL to approximately 1 μL.

The substrate concentration given in Example 1 (see below) provides one such case of a large excess of substrate, wherein the blocking substrate S is present at a concentration 1 mM that is large compared with the $K_S = 2$ μM dissociation binding constant for binding of the substrate of interest to the enzyme of interest. As implied by Equation (1) of Example 1, providing the blocking substrate at a concentration much larger than $K_S$ and much larger than the enzyme concentration E makes it difficult for a test ligand to displace the blocking substrate, thereby providing the desired effect.

Once placed on the nanocalorimeter cell, the drops may be merged by any known means that does not introduce significant differential heating between the measurement and reference sides, such as, for example, that described in Attorney Docket No. D/A1578Q, U.S. application Ser. No. 10/115, 336, "Apparatus and Method for Using Electrostatic Force to Cause Fluid Movement". Then measurements are performed to detect a heat of reaction on the measurement side, which is compared to the measurement taken for the combination of drops in the reference region. In the case of the embodiment in FIG. 1, the bridge measurement directly senses the difference in heat evolved in the measurement and reference regions, eliminating the need for an explicit comparison of the two.

Other means can also be used to bring the samples together, and are fully contemplated here and in the claims. For example, fluids may be brought together near the thermal sensors by application of electrical force, drop deposition, drop translation along a support, or either drop, continuous fluid, or fluid packet translation through a channel or channels, including fluidic channels fabricated in devices using, for example, MEMS, "soft lithography", or other biochip fabrication techniques. Also, in embodiments, drops may be introduced in ways that do introduce significant differential heating between the measurement and reference sides, as long as the signal is detected for a period that is long enough for the differential heating to dissipate. Such cases can occur, for example, when the heat is generated by an enzymatic reaction that runs for a time longer than the time for a pulse of mixing heat to dissipate from the detectors.

In this example embodiment, if the test compound such as a test ligand binds to a site other than the targeted site, then there normally will be little or no signal, as the binding will occur on both the measurement and reference sides to a comparable extent. However, if the test compound binds to the targeted site, then there normally will be a signal comparable to that expected for binding to the target compound, as long as the $K_L$ (dissociation constant) for the binding of test compound is not too small (i.e., too strong). In this case of differentiated binding to the targeted site, the targeted site is blocked in the reference region, whereas ligand binding will proceed unimpeded on the measurement side. Using this assay, one can directly screen a large compound library for binding to the targeted site, eliminating the problem of getting unwanted hits from ligands that bind to other sites. This type of measurement is not possible using techniques available today, such as antibody-based endpoint assays discussed hereinabove.

Figure 3:
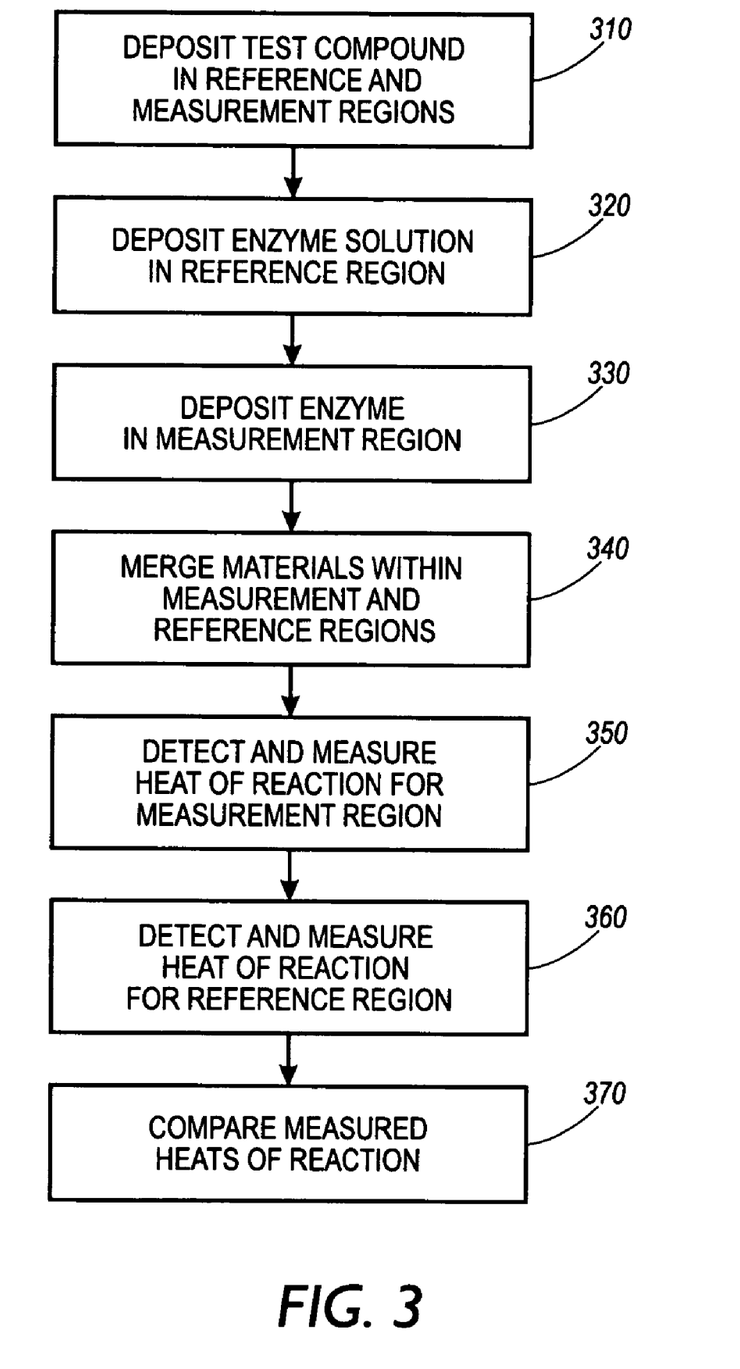
FIG. 3 is a diagram illustrating the embodiment of the method of FIG. 2.

The method for this example embodiment, screening for binding to a specific site on a target compound by looking with and without an agent that blocks the specific binding site, is summarized in FIG. 3. A solution of target compound, which in embodiments can be a solution of enzyme target compounds, is deposited in the measurement region of a nanocalorimeter at 310. At 320, a solution of target compound plus agent that blocks a binding site of interest, which in embodiments can be, for example, an enzyme target and a large excess of enzyme-specific substrate, is deposited in the reference region of a nanocalorimeter. Test compound, which may comprise a potential ligand, is deposited in each of the reference and measurement regions of a nanocalorimeter at 330. In embodiments, the drop on the reference region also contains the same concentration of blocking agent, for example, excess enzyme-specific substrate, as used in 320 to minimize heats of mixing. The deposition pattern for enzyme deposition 310, target compound deposition 320, and potential ligand deposition 330 may occur in any sequence or simultaneously.

The materials within the reference and measurement regions respectively are merged at 340. The drops may be merged by any known means that does not introduce significant differential heating between the measurement and reference sides, such as, for example, that described in Attorney Docket No. D/A1578Q, U.S. application Ser. No. 10/115, 336, "Apparatus and Method for Using Electrostatic Force to Cause Fluid Movement". The nanocalorimeter detects and measures any heat of reaction for the measurement region at 350 and detects and measures any heat of reaction for the reference region at 360. Detection and measurement of the heats of reaction may be performed by any known method, including that discussed with respect to FIG. 1 hereinabove, and may occur simultaneously or sequentially. The measured heats of reaction are then compared at 370. Additionally, a nanocalorimeter device may provide comparison of the heats of reaction directly, eliminating the need for separate measurements of heats of reactions. In the case of the nanocalorimeter embodiment depicted in FIG. 1, the heats of reaction are "compared" directly by the bridge configuration, that is, the bridge configuration of the thermal sensors directly detects the differential heating. This embodiment can minimize noise and therefore give higher sensitivity. In other embodiments, the heats of reaction are measured separately, recorded or temporarily stored by some means, and compared subsequent to the measurement.

Other means can also be used to bring the samples together, and are fully contemplated here and in the claims. For example, fluids may be brought together near the thermal sensors by drop deposition, drop translation along a support, or either drop, continuous fluid, or fluid packet translation through a channel or channels, including fluidic channels fabricated in devices using, for example, MEMS, "soft lithography", or other biochip fabrication techniques. Also, in embodiments, drops can be introduced in ways that do introduce significant differential heating between the measurement and reference sides, as long as the signal is detected for a period that is long enough for the differential heating from mixing to dissipate. Such cases can occur, for example, when the heat is generated by an enzymatic reaction that runs for a time longer than the time for a pulse of mixing heat to dissipate from the detectors.

There are cases in which a differential signal can occur without the test molecule binding to the same site as the blocking agent, such as cases in which blocking of a binding site in the reference region allosterically alters the target compound enough to significantly change the binding enthalpy of a test ligand at a site other than the targeted site. Such cases might result in a differential signal of large enough magnitude to be considered a hit in screening work, due to different binding heats for binding to blocked versus unblocked target compounds. In many cases, any such difference in binding enthalpy should be small, and in high-throughput screening, the number of cases that produce this effect should usually be small relative to the number of hits. In embodiments, cases where such allosteric effects are of concern and such allosteric binders need to be screened can be handled either by follow-up tests for allosteric binding or by adding blocking agent to the allosteric binding site to the measurement side of the differential measurement. As an example of an allosteric effect that can be important in drug screening, in some cases the binding of ATP can cause a conformational change to the active site on a kinase, essentially activating it for substrate binding and conversion. The activated state of the substrate binding site can bind substrate differently than the unactivated state, and it might be desired to find test ligands that bind specifically to the activated state.

The method described above, comprising addition of excess ATP to the measurement side, anticipates this case. With ATP added to the measurement side, the kinase will be in its activated state on that side, thereby enabling screening for ligand binding to the activated state, while at the same time eliminating false positives due to compounds binding to the ATP site. Follow-up measurements on test ligands that exhibit a positive signal can be done to determine whether the test ligand undergoes an enzyme-catalyzed reaction (e.g., phosphorylation) or simply binds. Hits of the former type would be useful as surrogate substrates, and hits of the latter type would be useful as hits and leads for drug development. In embodiments, if it is desired to avoid hits of the former type, then a non-hydrolyzable analog of ATP may be added instead of ATP to activate the enzyme without enabling ATP hydrolysis, thereby avoiding substrate turnover. Examples of non-hydrolyzable ATP analogs include adenylyl imidodiphosphate (AMP-PNP) and adenosine 5'-[γ-thio]triphosphate (ATP-γS).

In an embodiment, it may be desirable to have the kinase in the reference region also be "activated" by ATP, for example to minimize conformational differences between the enzymes in the measurement and reference regions. By minimizing such differences, one can reduce the number of hits due to allosteric binders that bind differently to activated vs. non-activated enzymes but do not bind at the targeted site. As can be appreciated by those experienced in drug discovery, in some cases it can be useful to minimize hits from such allosteric binders, whereas in other cases it can be useful to identify hits from such allosteric binders and consider them further as potential drug leads. The choice depends on the particular drug discovery activity. In the former case, activating the kinase in the reference region can be complicated when there is also substrate or surrogate substrate present in the reference region as a blocking agent. In such cases, it is desirable to prevent turnover of the substrate or surrogate substrate, as the turnover causes evolution of heat and eventually removes the blocking agent. In embodiments, a non-hydrolyzable analog of ATP may be added to the reference site to activate the enzyme without enabling ATP hydrolysis, thereby avoiding substrate turnover. Examples of non-hydrolyzable ATP analogs include adenylyl imidodiphosphate (AMP-PNP) and adenosine 5'-[γ-thio]triphosphate (ATP-γS).

As yet another example, consider the case of a kinase for which one is screening to find compounds that bind to an enzyme-specific substrate site, which is different from the ATP binding site. Using the enzyme-specific substrate that is phosphorylated by the kinase as the blocking agent on the reference side provides the method as described above, but in addition one can add an excess of ATP to the drops in the measurement side. Without the excess ATP, a test compound might bind to the ATP binding site on the measurement side with a higher enthalpy than on the reference side due to allosteric effects caused by the blocking agent, and it would then erroneously appear as a candidate for further consideration. However, the excess ATP further blocks binding to the ATP site on the measurement side, so such a test compound would now produce binding heat only on the reference side. As this would create a negative differential signal, the compound could be removed from further consideration as a drug hit or lead. In drug screening, binders with an exothermic enthalpy of binding are generally considered to be better hits or leads than binders with endothermic enthalpies of binding.

If the test compound binds so strongly to the ATP site that it displaces the ATP blocking agent in the measurement side, then there still will not be a positive differential heating, as binding will occur to the same extent on the reference side. In embodiments, a non-hydrolyzable analog of ATP may be added to the reference site to eliminate any binding to the ATP binding site on the reference side. Examples of non-hydrolyzable ATP analogs include adenylyl imidodiphosphate (AMP-PNP) and adenosine 5'-[γ-thio]triphosphate (ATP-γS).

Figure 4:
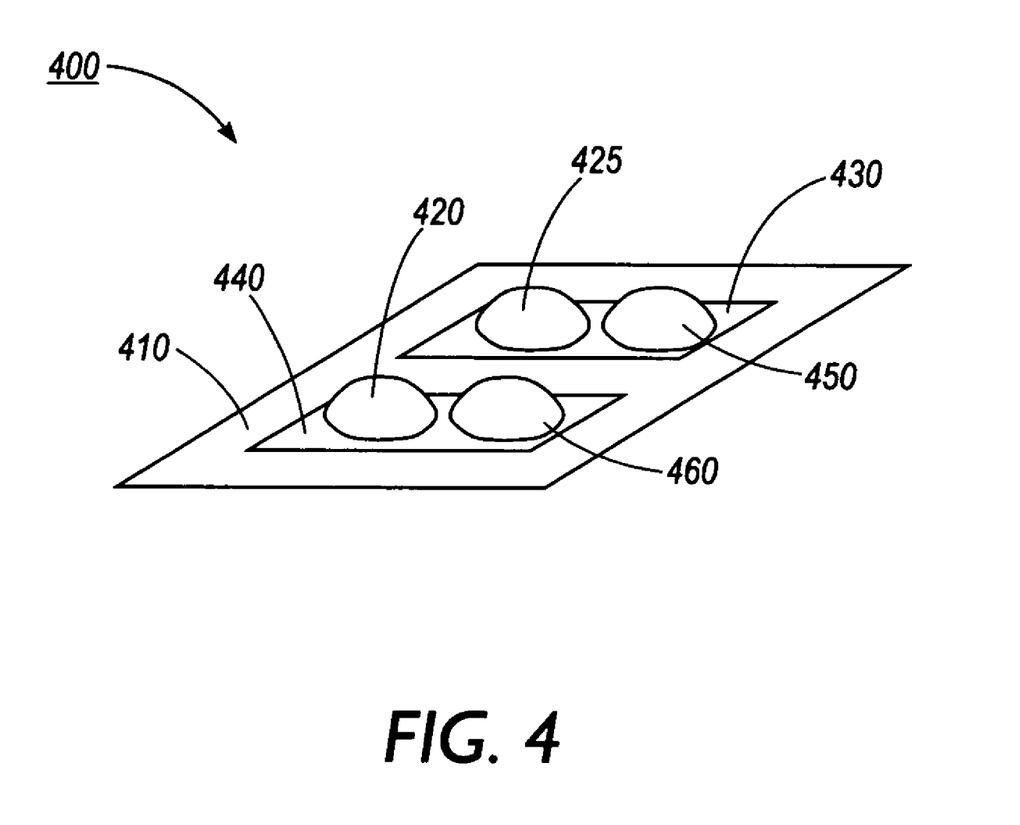
FIG. 4 is an illustration depicting enzyme and ligand drop deposition within a single cell of a testing array, according to another embodiment of the method.

In an embodiment of this test, depicted in FIG. 4, a drop 460 of target kinase that also contains an excess of ATP as a blocking agent, and a test ligand drop 420 with the same or nearly the same concentration of ATP, are deposited on the measurement side 440 of a nanocalorimeter cell. In addition, a reference drop 450 that contains the enzyme-specific substrate as a blocking agent and the same target kinase as drop 460 but is free of ATP, and a ligand drop 425 containing the same or nearly the same concentration of blocking agent as drop 450, are deposited on the reference side 430 of a nanocalorimeter cell. In embodiments, a non-hydrolyzable analog of ATP may be added to drops 450 and 425. In embodiments, a non-hydrolyzable analog of ATP may be used instead of ATP in drops 460 and 420. Both reference region 430 and measurement region 440 reside within thermal isolation region 410. The nanocalorimeter cell directly measures the difference in heating between the measurement and reference sides upon merging of the respective target compound and test compound drops. The drops may be merged by any known means that does not introduce significant differential heating between the measurement and reference sides, such as, for example, that described in Attorney Docket No. D/A1578Q, U.S. application Ser. No. 10/115,336, "Apparatus and Method for Using Electrostatic Force to Cause Fluid Movement". Measurement is performed to detect the heat evolved on the measurement side, which is compared to the measurement taken for the combination of drops in the reference region. If the measurement side generates more binding heat than the reference side, then the test compound is a candidate ligand for binding at a site other than the ATP binding site, as desired in this embodiment.

Figure 5:
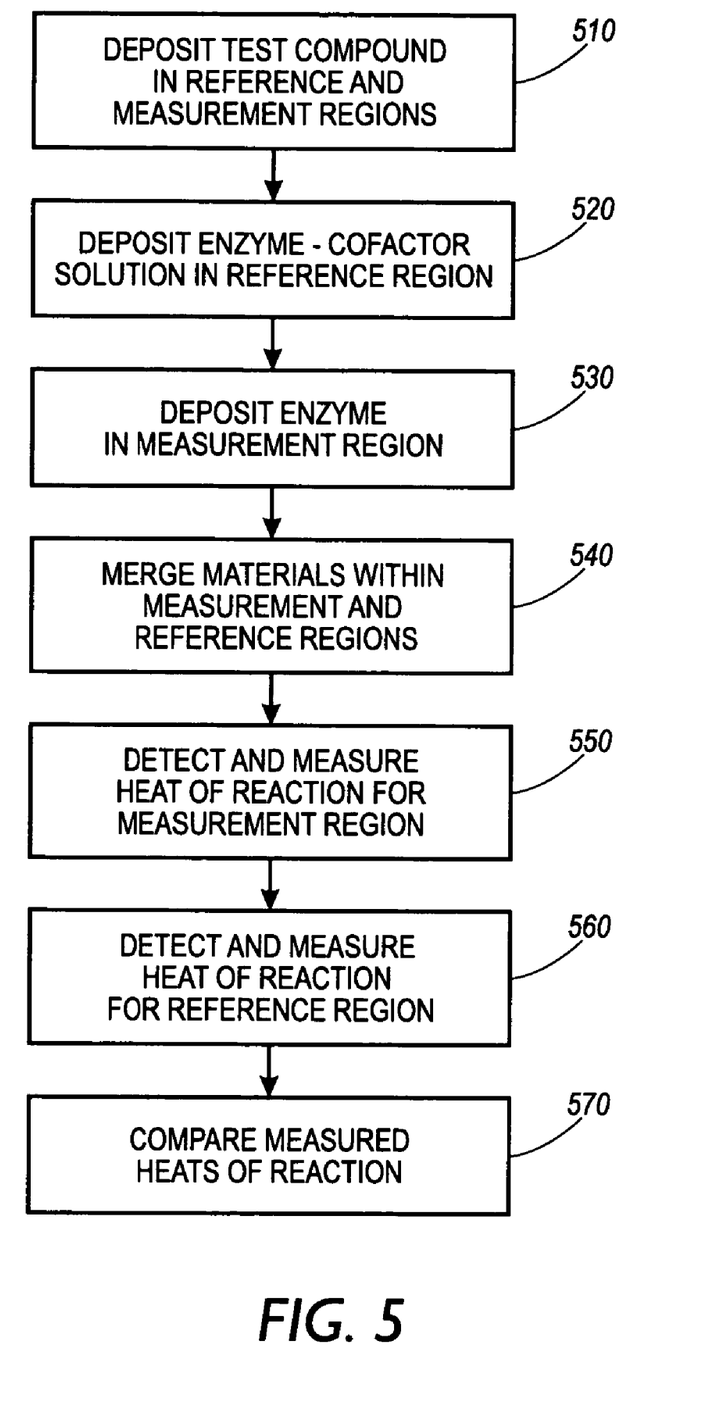
FIG. 5 is a diagram illustrating the embodiment of the method of FIG. 4.

The method for this embodiment, the identification of compounds that do not bind to the ATP site of a kinase but bind to or have binding that is significantly blocked by the kinase-specific substrate site, is summarized in FIG. 5. Drops containing test compound, which may be a potential ligand for the target compound, are deposited in each of the reference and measurement regions of a nanocalorimeter at 510. In embodiments, the drop with test compound on the reference side also contains the blocking agent used on the reference side, for example, an excess concentration of the kinase-specific substrate. In embodiments, the drop on the measurement side contains the ATP blocking agent, which may be at a concentration that minimizes or eliminates the heat of mixing due to differences in ATP concentration. Buffer conditions, such as pH, may also be closely matched to minimize heats of mixing in the presence of ATP salts. A solution of target compound and blocking agent, which in embodiments is a drop of enzyme in an excess of enzyme-specific substrate, is deposited within a nanocalorimeter reference region at 520. In embodiments, the drop contains the same or nearly the same concentration of blocking agent, such as the kinase-specific substrate, used in the corresponding test compound drop in 510, in order to minimize differential heats of mixing.

At 530 a drop of target compound with excess ATP is deposited in the measurement region of a nanocalorimeter. In embodiments, the drop contains the same or nearly the same concentration of ATP used in the corresponding test compound drop in 510, in order to minimize differential heats of mixing. Again, it is important to match buffer conditions, such as pH, in addition to matching ATP concentration, in order to minimize differential heats of mixing. The materials within the reference and measurement regions respectively are merged at 540. The drops may be merged by any known means that does not introduce significant differential heating between the measurement and reference sides, such as, for example, that described in Attorney Docket No. D/A1578Q, U.S. application Ser. No. 10/115,336, "Apparatus and Method for Using Electrostatic Force to Cause Fluid Movement". The nanocalorimeter detects and measures any heat evolved for the measurement region at 550 and detects and measures any heat evolved for the reference region at 560. Detection and measurement of the heats of reaction may be performed by any known method, including that discussed with respect to FIG. 1 hereinabove, and may occur either simultaneously or sequentially. The measured heats of reaction are then compared at 570. The deposition pattern for enzyme deposition 510, target compound deposition 520, and potential ligand deposition 530 may occur in any sequence or simultaneously.

In embodiments, a confirmation screen after the initial screen of test compounds can be used to examine properties of the initial hits. For example, in the case of enzyme targets in drug screening, it might be of interest to know whether a test compound will act as an inhibitor, regulator, or perhaps undergo a reaction catalyzed by the enzyme target. Confirmation measurements after the initial screen with substrate, any necessary cofactors, and the test compound that showed binding in the initial screen will provide data on the increase or decrease in enzymatic reaction due to the presence of the test compound. There is also the possibility that a test compound may bind endothermically in the reference region in the presence of blocking agent but not bind in the measurement region, giving a positive differential signal. Confirmation screens can be used to identify such false positives.

The blocking of binding at a site, for example a substrate site, by the presence of blocking agent, for example excess substrate, becomes less effective if the ligand binds at much lower dissociation constant $K_L$ than substrate $K_S$, leading to the lower limit mentioned hereinabove. As an example, discussed with reference to Example 1 below, consider a substrate with $K_S=2$ μM used as a blocking agent, and the concentrations and conditions listed in Example 1 below. For this case, a practical value for the lower limit of the ligand dissociation constant, below which the screen will give a false negative, may be approximately $K_L=1$ nM, assuming the lower limit of $10\mu°$ C. for detection with the nanocalorimeter used for the example. False negatives at $K_L<1$ nM should not be a concern in many cases, as it is rare to find such strong binders in the initial high-throughput screening of drug targets. As discussed below, one can also reduce the lower limit further by performing a preliminary screen to identify a tighter binding substrate for blocking the binding site of interest.

As a counter-example, consider Example 2. In that example, the substrate $K_S$ equals 100 μM. Since the substrate binding is weaker, it is not as good of a blocking agent. As example 2 discusses, this example blocking agent becomes ineffective at $K_L$ below about 25 nM, increasing the possibilities of false negatives relative to example 1. For this example, it might be desired to have a larger signal at the lower values of $K_L$. In such a case, a preliminary screen may be performed, for example with nanocalorimeter arrays, to find a surrogate substrate or simple binder that binds at $K_S \leq 2$ μM, rather than at 100 μM, thereby reducing the lower limit of detectable $K_L$'s to about 1 nM or less, as described in Example 1 above.

In embodiments, surrogate substrates can be used to block binding to the corresponding substrate binding site on an enzyme target of interest. Surrogate substrates play an important role in drug discovery with enzyme targets. The endpoint assays in use today require a substrate that is catalyzed and a method to recognize the completion of the reaction. Generally, surrogate substrates (small peptides, 20 to 60 amino acids in length) serve as the substrate for assays because natural substrates are difficult to isolate with full activity, in addition to often being available only in limited quantities. In addition, natural substrates tend to be relatively large molecules, and many of the widely used readout formats, i.e., FP and FCS, require a reaction between small molecules because they rely on subsequent differentiation with product size. For the purposes of this invention, natural substrates often have relatively large values of $K_S$ relative to the values needed to be a good blocking agent. Using surrogate substrates that are stronger binders, i.e., have lower $K_S$, can be useful.

Surrogate substrates can be chemically designed from an understanding of the enzyme and its natural substrate. The protein sequences for these molecules are often starting points, and surrogates are constructed by iterative modification. Often, generic sequences for specific classes of enzyme are starting points for new enzymes in that class. The goal is to make surrogates react rapidly in the presence of enzyme. If desired, nanocalorimeter arrays or other high-throughput techniques can be used to screen compounds in the process of designing new surrogate substrates.

In embodiments, compounds in a library of test surrogate substrates are combined with an enzyme and any necessary co-substrates or cofactors, and the heat evolved is measured. This heat can be measured relative to a reference, such as in a nanocalorimeter measurement with both a measurement and reference side, or the heat can be measured directly when the enzyme and test surrogate substrate concentrations are sufficiently high. If the test surrogate substrate turns out to actually be a substrate for the enzyme of interest, then the experiment with that test substrate will evolve heat, identifying the test substrate as a candidate for use as a surrogate substrate in enzyme assays, or as a candidate for further modification into a suitable surrogate substrate. In embodiments, the test substrates can be selected or designed based on knowledge of substrates for similar enzymes, as discussed above. Using nanocalorimetry to screen for and develop surrogate substrates eliminates the need for an endpoint assay and the corresponding method for recognizing the reacted substrate. Using nanocalorimetry to screen for and develop surrogate substrates also provides a generic method, insofar as the heat evolved can be measured with nanocalorimetry, without the need for antibody recognition and binding, fluorescent or spectroscopic measurements, or other detection methods that may be more specific to certain classes of test compounds.

In embodiments involving enzymatic targets, a possibility is that a test ligand binds to a cofactor or co-substrate site in the reference region of the initial screen and actually undergoes a reaction with the substrate or surrogate substrate being used as a blocking agent. Such cases may be identified, since there will be more heat generation on the reference side than on the measurement side, and when this happens the test ligand is not of interest. (This change in sign of the signal can also occur if a test ligand binds to the substrate side endothermically, but test ligands that bind endothermically are generally not of interest as leads in drug development.)

In some cases and embodiments, it is desirable to find inhibitors that bind to a specific cofactor or regulator site rather than a substrate site. For example, many enzymes are inhibited by the product of either their reaction or a reaction further downstream, an example being inhibition of a kinase by the phosphorylated substrate of that kinase. (A well known example is hexokinase, which is weakly inhibited by its product glucose-6-phosphate.) Binding at such regulatory sites could be much more specific to that enzyme than binding of cofactors like ATP, so that site could be an attractive site for drug targeting, in some cases. In embodiments, the method described above can be used to target the regulatory site, for example by introducing the natural inhibitor/product instead of excess substrate on the reference side to block the regulatory binding site. Similar techniques could be used to target effector sites, which may be desirable when the effectors are enzyme-specific.

In yet another embodiment, it is desired to screen a library of test compounds to find hits that bind to a site on a target other than some previously targeted site, a strongly binding ligand having been previously identified for the said previously targeted site. An example is the case of an ATP kinase that has a known, strongly binding ligand that binds to the ATP binding site, but in a non-specific manner. Such a ligand could have been discovered in earlier screening work with the kinase, for example, only to find that the lack of binding specificity rendered the ligand of little value as a drug lead. Now an investigator might want to re-screen the drug target against a library of test ligands, while desiring to find hits that bind only at sites other than the ATP binding site. In this embodiment, the previously identified ligand that binds strongly at the ATP binding site is used as the blocking agent in practicing the current disclosure. In this example, the blocking agent is used in the measurement side of a nanocalorimeter, to block binding at the corresponding site on the target compound, and no blocking agent is used in the reference side. An exothermic signal then corresponds to a new ligand that binds in the presence of the previously-identified ligand.

In some cases, the new ligand can then be used to develop an entirely new drug lead or compound. In other cases, it may be desired to find a ligand that binds in the presence of the previously-identified ligand, for the purposes of using the new ligand as a candidate for conjugation to the previously-identified ligand. Conjugation of the new ligand and the previously-identified ligand may then be used to develop a drug lead that has both strong binding and the required specificity.

Consider, for example, the concentrations in Example 3. For this example, a drop of test ligand with blocking agent and a second drop of the target compound with blocking agent are deposited on the measurement side of a nanocalorimeter, in accordance with the embodiment just discussed. A drop of test ligand with blocking agent and a second drop with blocking agent, but no target compound, are deposited on the reference side. The buffers are also closely matched to minimize heats of mixing. The drops are merged and the differential heating is measured. If there is differential heating, then the test ligand is a hit for binding to a site other than the blocked site, assuming common mode heating effects, such as heats of mixing, have been properly controlled in the experiment. If this occurs, the ligand is identified for further investigation as a possible drug lead, either alone or in conjugation with the blocking agent. In embodiments, when the binding is strong enough to be detectable without the common mode rejection afforded by the reference side of the above measurements, then the detection can be done without requiring a detector having a reference region.

In yet another embodiment, measurements with multiple blocking agents can be performed to more efficiently screen for binding to more than one identified site. For example, consider an enzyme target having a cofactor site and a regulator site in addition to two substrate sites, and consider the case wherein it is desired to find ligands that bind to the first substrate site, the cofactor site, or the regulator site, but not to the second substrate site. In a first set of experiments, test ligands are screened against enzyme target, with blocking agents of the first substrate site, the cofactor site, and the regulator site all present in the solutions in the reference region of a device, said device having both a measurement and reference region. Additionally, a blocking agent for the second substrate site is present in the solutions in the measurement region. More generally, sites which are targeted for binding are all blocked in the reference region, and sites for which binding is not desired are all blocked in the measurement region. When the test ligands are tested, the ones that give a positive signal for binding in the measurement region are candidate ligands for binding to one of the preferred sites, and follow-up tests can be performed to determine the specific binding site of any particular one of these ligands. As an example of a follow-up test, the blocking agent for the cofactor site can be moved to the measurement region and a second set of experiments performed on positive hits from the first set of experiments. Ligands that show a reversal in the sign of the heat of reaction would then be identified as ligands to the cofactor site, and ligands that do not show a reversal in the sign of the heat of reaction would be identified as ligands to either the regulator site or the first substrate site. Subsequent tests can obviously be used to further distinguish binding to the regulator site versus binding to the first substrate site.

The advantage to this embodiment is significant when targets have multiple binding sites of interest and screening tests are expected to give a low percentage of hits. If, for example, one screens a million compounds for binding to three different sites by blocking one site at a time, then three million screening events are required. If instead one practices this embodiment and screens the one million compounds for binding to any of the three sites, and 0.1% of the compounds are hits, then all 1,000 (0.1% of 1,000,000) of the hits are identified after one million screening events. In this second case, only a maximum of 3000 more screening events are needed to identify which binding site corresponds to each hit.

EXAMPLES

In the first two examples, consider the binding of a substrate S and competitive binding of a ligand L to an enzyme E.

Example 1

Calculation for competitive binding of substrate S and test ligand L to enzyme E. Conditions are such that the substrate does not undergo reaction. For example, E could be an ATP kinase, S a substrate, and no ATP is provided; the substrate will not become phosphorylated because the ATP is absent. Optionally, a non-hydrolyzable ATP analog could be present, such as adenylyl imidodiphosphate (AMP-PNP) or adenosine 5'-[γ-thio]triphosphate (ATP-γ-S). Binding of substrate to enzyme ($K_S$ is the dissociation equilibrium constant) is modeled by the following reaction, where E is free enzyme, S is free substrate, and E·S is enzyme E with substrate S bound to it:

$$E + S \rightarrow E \cdot S \tag{1}$$

-continued $$K_S = \frac{[E][S]}{[E \cdot S]}$$

Binding of test ligand to enzyme ($K_L$ is the dissociation equilibrium constant) is modeled by the following reaction, where E is free enzyme, L is free test ligand, and E·L is enzyme E with test ligand L bound to it:

$$E + L \rightarrow E \cdot L \quad (2)$$

$$K_L = \frac{[E][L]}{[E \cdot L]}$$

In these equations, square brackets denote molar concentrations. The species E, S, and L also obey mass balance equations:

$$E_0 = [E] + [E \cdot S] + [E \cdot L] \quad (3)$$

$$S_0 = [S] + [E \cdot S] \quad (4)$$

$$L_0 = [L] + [E \cdot L] \quad (5)$$

In equations 3-5, $E_0$ and $L_0$ are the total molar concentrations of enzyme and ligand, respectively, in the combined drops in both the measurement and reference regions, including both bound and unbound species, and $S_0$ is the total concentration of substrate in the combined drop in the reference region, including both bound and free substrate. Equation (3) assumes S and L compete for binding at the same site and cannot both bind an enzyme molecule at the same time. Equations 1-5 can be solved to determine the amount of bound ligand L and substrate S in both the measurement and reference regions of a measurement device, and the molar enthalpy of binding can then be multiplied by the concentration of bound species to determine the temperature signal, ΔΔT. The term ΔΔT is the difference between ΔT in the measurement region and ΔT in the refernce region.

Consider the following conditions:
$K_S$=2 μM for binding of substrate to enzyme
$S_0$=total concentration of substrate=1 mM
$E_0$=total concentration of enzyme=5 μM
$L_0$=total concentration of test ligand=7.5 μM
$\Delta H_L$=−10 kcal/mole for binding of ligand to enzyme
$\Delta H_S$=−1 kcal/mole for binding of substrate to enzyme For these parameter values, Table 1 lists the calculated differential signal to be expected as a function of $K_L$, the dissociation constant for the test ligand. The differential signal corresponds to the enthalpy from binding of ligand L to enzyme E in the absence of blocking substrate S($S_0$=0), minus the enthalpy from binding of ligand L in the presence of the above concentration of S, namely, $S_0$=1 mM, as blocking agent. For test ligands in high-throughput screening, $K_L$ is not usually known beforehand, so Table 1 indicates what range of $K_L$ will yield hits in a screening study. For the purposes of this example, assume that a hit is a measurement with a differential temperature rise upon binding of >10μ° C.

TABLE 1

| $K_L$ (dissociation constant for ligand) vs. Signal | |
|---|---|
| $K_L$ | ΔΔT |
| 20 μM | 11.9 μ° C. |

TABLE 1-continued

| $K_L$ (dissociation constant for ligand) vs. Signal | |
|---|---|
| $K_L$ | ΔΔT |
| 5 μM | 24.9 μ° C. |
| 2 μM | 33.4 μ° C. |
| 1 μM | 38.4 μ° C. |
| 500 nM | 41.9 μ° C. |
| 200 nM | 43.7 μ° C. |
| 50 nM | 39.8 μ° C. |
| 20 nM | 33.3 μ° C. |
| 5 nM | 21.4 μ° C. |
| 2 nM | 14.8 μ° C. |
| 1 nM | 11.1 μ° C. |

Example 2

Competitive binding of substrate S and test ligand L to enzyme E at higher $K_S$. At larger $K_S$, the substrate is not as effective at blocking binding by a test compound to the substrate site.

Consider the following conditions:
$K_S$=100 μM for binding of substrate to enzyme
$S_0$=total concentration of substrate=2 mM
$E_0$=total concentration of enzyme=5 μM
$L_0$=total concentration of test ligand=7.5 μM
$\Delta H_L$=−10 kcal/mole for binding of ligand to enzyme
$\Delta H_S$=−1 kcal/mole for binding of substrate to enzyme For these parameter values, Table 2 lists the calculated differential signal to be expected as a function of $K_L$, the dissociation constant for the test ligand. For test ligands in high-throughput screening, $K_L$ is not usually known beforehand, so Table 2 indicates what range of $K_L$ will yield hits in a screening study. Whereas the substrate in Example 1 will block test ligands down to about $K_L$=1 nM, the substrate in this example will only block down to about $K_L$=25 nM, resulting in a larger possibility of false negatives.

TABLE 2

| $K_L$ (dissociation constant for ligand) vs. Signal | |
|---|---|
| $K_L$ | ΔΔT |
| 20 μM | 11.2 μ° C. |
| 5 μM | 22.1 μ° C. |
| 2 μM | 27.4 μ° C. |
| 1 μM | 28.7 μ° C. |
| 500 nM | 27.3 μ° C. |
| 200 nM | 22.6 μ° C. |
| 100 nM | 18.3 μ° C. |
| 50 nM | 14.2 μ° C. |
| 25 nM | 10.8 μ° C. |

Example 3

In the following example, consider the binding of a blocking agent B (e.g., a previously identified ligand for a particular binding site) and simultaneous binding of a ligand L to an enzyme E. In this example, we are screening for binders to sites other than the binding site for the blocking agent B, which is the opposite of the case in Examples 1 and 2. In the measurement region of a nanocalorimeter or other measuring device, we combine a drop of enzyme and blocking agent with a drop of test ligand and blocking agent. In the reference region, we combine a drop of blocking agent (no enzyme)

with a drop of blocking agent and test ligand. The nanocalorimeter measures the difference in heat generated in the measurement versus reference regions. Conditions are such that the blocking agent does not undergo enzymatic reaction.

Binding of blocking agent to enzyme ($K_B$ is the dissociation equilibrium constant for the blocking agent) is modeled by the following reaction, where E is free enzyme, B is free blocking agent, and E·B is enzyme E with blocking agent B bound to it:

$$E + B \rightarrow E \cdot B \qquad (6)$$

$$K_B = \frac{[E][B]}{[E \cdot B]}$$

Binding of test ligand to enzyme ($K_L$ is the dissociation equilibrium constant for the test ligand) is modeled by the following reaction, where E is free enzyme, L is free test ligand, and E·L is enzyme E with test ligand L bound to it:

$$E + L \rightarrow E \cdot L \qquad (7)$$

$$K_L = \frac{[E][L]}{[E \cdot L]}$$

In these equations, square brackets denote molar concentrations. Equation (7) assumes L does not bind to E when B is already bound, hence it describes the competitive binding case. In cases where the species B and L compete perfectly for binding to E at the same site, the species E, B, and L also obey mass balance equations:

$$E_0 = [E] + [E \cdot B] + [E \cdot L] \qquad (8)$$

$$B_0 = [B] + [E \cdot B] \qquad (9)$$

$$L_0 = [L] + [E \cdot L] \qquad (10)$$

In equations 8-10, $E_0$ is the total molar concentrations of enzyme in the combined drop in the measurement region, including both bound and unbound species, and $L_0$ and $B_0$ are the total concentration of test ligand and blocking agent in the combined drops in both the measurement and reference regions, including both bound and free species. Equation (8) follows because either B or L can bind to the site that B is "blocking", but not both at the same time. Equations 6-10 can be solved to determine the amount of bound ligand L and blocking agent B, and the molar enthalpy of binding can then be multiplied by the concentration of bound species to determine the temperature signal for competitive binding.

For binding of L to E independent of B, the corresponding equations are $$E' + L \rightarrow E' \cdot L \qquad (11)$$

$$K_L = \frac{[E'][L]}{[E' \cdot L]}$$

$$E_0 = [E'] + [E' \cdot L] \qquad (12)$$

$$L_0 = [L] + [E' \cdot L] \qquad (13)$$

where E' is free E plus E bound to B but not L. Equations 11-13 can be solved to determine the amount of bound ligand L, and the molar enthalpy of binding can then be multiplied by the concentration of bound species to determine the temperature signal for independent binding.

Consider the following conditions:
$K_B$=20 nM for binding of substrate to enzyme
$B_0$=total concentration of blocking agent=1 mM
$E_0$=total concentration of enzyme=5 µM
$L_0$=total concentration of test ligand=7.5 µM
$\Delta H_L$=−10 kcal/mole for binding of ligand to enzyme
$\Delta H_B$=−12 kcal/mole for binding of blocking agent to enzyme In this example, $K_B$ is relatively low at 20 nM. Such a value is reasonable for a blocking agent that is a previously identified strong binder to a drug target, including the case of a strongly binding ligand discovered and optimized in a drug screening operation but found to not be sufficiently specific to the target of interest. For these parameter values, Table 3 lists the calculated differential signal to be expected as a function of $K_L$, the dissociation constant for the test ligand. The differential signal corresponds to the enthalpy from binding of ligand L to enzyme E in the presence of blocking agent B ($B_0$=1 mM) in the measurement region of a test device, minus the enthalpy from mixing of ligand L with blocking agent B, in the absence of enzyme E, in the reference region of a nanocalorimeter test device. For test ligands in high-throughput screening, $K_L$ is not usually known beforehand, so Table 3 indicates what range of $K_L$ will yield hits in a screening study, which in this example is a binding interaction with a differential temperature of >10µ° C.

TABLE 3

$K_L$ (dissociation constant for ligand) vs. Signal

| $K_L$ | ΔΔT, L binds to same site as B | ΔΔT, L binds independent of B binding |
|---|---|---|
| 20 µM | ≈0 µ° C. | 12.0 µ° C. |
| 5 µM | ≈0 µ° C. | 25.0 µ° C. |
| 2 µM | ≈0 µ° C. | 33.7 µ° C. |
| 1 µM | ≈0 µ° C. | 39.1 µ° C. |
| 500 nM | ≈0 µ° C. | 43.2 µ° C. |
| 200 nM | ≈0 µ° C. | 46.7 µ° C. |
| 50 nM | ≈0 µ° C. | 49.1 µ° C. |
| 20 nM | ≈0 µ° C. | 49.6 µ° C. |
| 5 nM | −0.3 µ° C. | 49.9 µ° C. |
| 2 nM | −0.7 µ° C. | 50.0 µ° C. |
| 1 nM | −1.2 µ° C. | 50.0 µ° C. |
| 0.5 nM | −2.1 µ° C. | 50.0 µ° C. |

As can be seen in Table 3, in this example all binders with $K_L$>0.5 nM that also bind independently of B (e.g., at a different site) will yield positives in a screening test, while comparably strong binders that bind at the same site as B will test negative. Ligands that have binding constants lower than 0.5 nM can give false negatives, but this risk is not too great in drug screening because hits from primary screening with dissociation constants lower than 0.5 nM are very rare.

While the present discussion has been illustrated and described with reference to specific embodiments, further modification and improvements will occur to those skilled in the art. It is to be understood, therefore, that this disclosure is not limited to the particular forms illustrated and that it is intended in the appended claims to embrace all alternatives, modifications, and variations which do not depart from the spirit and scope of the embodiments described herein.

The claims, as originally presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants/patentees and others.

What is claimed is:

1. A method for screening of compounds for binding differentiation at various drug target binding sites, for use with a device measuring the enthalpy of reaction for such binding, comprising:
   merging not less than one test ligand with not less than one target compound at not less than one first location on the device measuring enthalpy of reaction, wherein said target compound includes not less than one binding site of interest and not less than one binding site to be avoided;
   merging not less than one test ligand with not less than one target compound in the presence of at least one first blocking agent at not less than one second location on the device measuring enthalpy of reaction, wherein said target compound includes not less than one binding site of interest and not less than one binding site to be avoided;
   detecting a first heat of reaction for said merged not less than one test ligand and said not less than one target compound at said first location;
   detecting a second heat of reaction for said merged not less than one test ligand with said not less than one target compound in the presence of a blocking agent at said second location;
   comparing said first and second heats of reaction; and
   determining a binding operation has occurred at the binding site of interest of the first location when the comparing step finds the first heat of reaction is greater than the second heat of reaction.

2. The method for screening of compounds according to claim 1, wherein said at least one first blocking agent comprises a site-specific agent.

3. The method for screening of compounds according to claim 1, wherein said at least one first blocking agent comprises an excess of an enzyme specific substrate.

4. The method for screening of compounds according to claim 1, wherein said not less than one target compound comprises an enzyme target solution.

5. The method for screening of compounds according to claim 1, wherein said target compound and said test ligand at said not less than one first location are in the presence of at least one second blocking agent.

6. The method for screening of compounds according to claim 5, wherein said at least one second blocking agent comprises a cofactor solution and said at least one first blocking agent comprises an enzyme specific substrate solution.

7. The method for screening of compounds according to claim 5, wherein said at least one first blocking agent comprises a plurality of differing blocking agents.

8. The method for screening of compounds according to claim 7, wherein said plurality of differing blocking agents comprise an enzyme specific substrate solution and a regulatory agent solution.

9. The method for screening of compounds according to claim 7, wherein said plurality of differing blocking agents comprise an excess of enzyme specific substrate and a non-hydrolyzable nucleotide phosphate analog solution.

10. The method for screening of compounds according to claim 5, wherein said target compound comprises not less than one kinase target.

11. The method for screening of compounds according to claim 10, wherein said not less than one second blocking agent comprises an excess of ATP.

12. The method for screening of compounds according to claim 10, wherein said not less than one first blocking agent comprises a kinase specific substrate.

13. The method for screening of compounds according to claim 5, wherein said at least one second blocking agent comprises a plurality of differing blocking agents.

14. The method for screening of compounds according to claim 13, wherein said plurality of differing blocking agents comprise a cofactor and a regulatory agent solution.

15. The method for screening of compounds according to claim 1, wherein merging comprises application of electrostatic force.

16. The method for screening of compounds according to claim 1, wherein merging comprises drop deposition.

17. The method for screening of compounds according to claim 1, wherein merging comprises drop translation along a support.

18. The method for screening of compounds according to claim 1, wherein merging comprises fluid packet translation through not less than one channel.

19. The method for screening of compounds according to claim 1, wherein merging comprises continuous fluid translation through not less than one channel.

20. The method for screening of compounds according to claim 1, wherein merging comprises drop translation through not less than one channel.

21. The method for screening of compounds according to claim 7, wherein all said at least one preferred binding sites are blocked at said not less than one second location on the device.

22. The method for screening of compounds according to claim 13, wherein all said not less than one binding sites to be avoided are blocked at said not less than one first location on the device.

23. The method for screening of compounds according to claim 21, wherein all said preferred binding sites are blocked in said second location on the device and all said binding sites to be avoided are blocked in said first location on the device.

24. The method for screening of compounds according to claim 23, wherein alternate preferred binding sites are selected to be blocked in said second location on the device and alternate binding sites to be avoided are selected to be blocked in said first location of the device.

25. The method for screening of compounds according to claim 1, further comprising performing a preliminary screening for a surrogate substrate.

26. A method for screening of compounds for binding differentiation at various drug target binding sites, for use with a nanocalorimetric device measuring the enthalpy of reaction for such binding, wherein said nanocalorimetric device includes thermal isolation regions, reference regions, and measurement regions, the method comprising:
   depositing not less than one drop of a target compound within not less than one measurement region, wherein said target compound includes not less than one binding site of interest and not less than one binding site to be avoided;
   depositing not less than one drop of a target compound within not less than one reference region, wherein said target compound includes not less than one binding site of interest and not less than one binding site to be avoided;
   depositing not less than one drop of test compound within not less than one measurement region;
   depositing not less than one drop of test compound within not less than one reference region;

merging said target compound with said test compound in the presence of at least one first blocking agent within the not less than one reference region;

merging said target compound with said test compound within the not less than one measurement region;

detecting a first heat of reaction for said merged target compound and said test compound in the presence of said at least one blocking agent within the not less than one reference region;

detecting a second heat of reaction for said merged target compound and said test compound within the not less than one measurement region;

comparing said heats of reaction for the not less than one reference region and the not less than one measurement region; and determining a binding operation has occurred between said merged target compound and said test compound within the not less than one measurement region when the comparing step finds the second heat of reaction is greater than the first heat of reaction.

27. The method for screening of compounds for binding differentiation at various drug target binding sites according to claim 26, wherein said at least one first blocking agent comprises a site-specific agent.

28. The method for screening of compounds for binding differentiation at various drug target binding sites according to claim 26, wherein said at least one first blocking agent comprises an excess of an enzyme specific substrate.

29. The method for screening of compounds for binding differentiation at various drug target binding sites according to claim 26, wherein said not less than one drop of a target compound comprises an enzyme target solution.

30. The method for screening of compounds for binding differentiation at various drug target binding sites according to claim 26, wherein said test ligand and said target compound are in the presence of at least one second blocking agent within said measurement region.

31. The method for screening of compounds for binding differentiation at various drug target binding sites according to claim 29, wherein said at least one second blocking agent comprises a cofactor solution and said at least one first blocking agent comprises an enzyme specific substrate solution.

32. The method for screening of compounds for binding differentiation at various drug target binding sites according to claim 29, wherein said first blocking agent comprises a plurality of blocking agents.

33. The method for screening of compounds for binding differentiation at various drug target binding sites according to claim 31, wherein said plurality of blocking agents comprise enzyme specific substrate solution and regulatory agent solution.

34. The method for screening of compounds for binding differentiation at various drug target binding sites according to claim 32, wherein said plurality of blocking agents include an excess of enzyme specific substrate and a non-hydrolyzable nucleotide phosphate analog solution.

35. The method for screening of compounds for binding differentiation at various drug target binding sites according to claim 29, wherein said target compound comprises not less than one kinase target solution.

36. The method for screening of compounds for binding differentiation at various drug target binding sites according to claim 35, wherein said second blocking agent comprises an excess of ATP.

37. The method for screening of compounds for binding differentiation at various drug target binding sites according to claim 36, wherein said first blocking agent comprises a kinase-specific substrate.

38. The method for screening of compounds for binding differentiation at various drug target binding sites according to claim 32, wherein said at least one second blocking agent comprises a plurality of differing blocking agents.

39. The method for screening of compounds for binding differentiation at various drug target binding sites according to claim 26, wherein merging comprises application of electrostatic force.

40. The method for screening of compounds for binding differentiation at various drug target binding sites according to claim 26, further comprising performing a preliminary screening for a surrogate substrate.

41. The method for screening of compounds for binding differentiation at various drug target binding sites according to claim 27, wherein said drops have a drop size, said drop size ranging from approximately 100 pL to approximately 100 µL.

42. The method for screening of compounds for binding differentiation at various drug target binding sites according to claim 32, wherein all said at least one preferred binding sites are blocked at said not less than one reference region.

43. The method for screening of compounds for binding differentiation at various drug target binding sites according to claim 38, wherein all said not less than one binding sites to be avoided are blocked at said not less than one measurement region.

44. The method for screening of compounds according to claim 38, wherein said plurality of differing blocking agents comprise a cofactor and a regulatory agent solution.

45. The method for screening of compounds according to claim 42, wherein all said preferred binding sites are blocked in said reference region and all said binding sites to be avoided are blocked in said measurement region.

46. The method for screening of compounds according to claim 45, wherein alternate preferred binding sites are selected to be blocked in said reference region and alternate binding sites to be avoided are selected to be blocked in said measurement region.

47. The method for screening of compounds for binding differentiation at various drug target binding sites according to claim 26, wherein merging comprises application of electric force.

48. The method for screening of compounds according to claim 1, wherein merging comprises application of electric force.

49. A method for screening of compounds for binding differentiation at various drug target binding sites, for use with a device measuring the enthalpy of reaction for such binding, wherein said device includes thermal isolation regions, reference regions, and measurement regions, the method comprising:

depositing not less than one drop of a target compound within not less than one measurement region, wherein said target compound includes not less than one binding site of interest and not less than one binding site to be avoided;

depositing not less than one drop of a target compound within not less than one reference region, wherein said target compound includes not less than one binding site of interest and not less than one binding site to be avoided;

depositing not less than one drop of test compound within not less than one measurement region;

depositing not less than one drop of test compound within not less than one reference region;

merging said target compound with said test compound in the presence of at least one first blocking agent within the not less than one reference region;

merging said target compound with said test compound within the not less than one measurement region;

detecting a first heat of reaction for said merged target compound and said test compound in the presence of said at least one blocking agent within the not less than one reference region;

detecting a second heat of reaction for said merged target compound and said test compound within the not less than one measurement region;

comparing said heats of reaction for the not less than one reference region and the not less than one measurement region; and determining a binding operation has occurred between said merged target compound and said test compound within the not less than one measurement region when the comparing step finds the second heat of reaction is greater than the first heat of reaction.

* * * * *